US010576071B2

(12) United States Patent
Czarnik

(10) Patent No.: US 10,576,071 B2
(45) Date of Patent: Mar. 3, 2020

(54) DEUTERIUM-ENRICHED PIOGLITAZONE

(71) Applicant: Poxel SA, Lyons (FR)

(72) Inventor: Anthony W. Czarnik, Reno, NV (US)

(73) Assignee: Poxel SA, Lyons (FR)

(*) Notice: Subject to any disclaimer, the term of this patent is extended or adjusted under 35 U.S.C. 154(b) by 0 days.

(21) Appl. No.: 15/917,983

(22) Filed: Mar. 12, 2018

(65) Prior Publication Data

US 2019/0008842 A1    Jan. 10, 2019

Related U.S. Application Data

(60) Division of application No. 15/088,472, filed on Apr. 1, 2016, now Pat. No. 9,925,175, which is a continuation of application No. 14/272,761, filed on May 8, 2014, now abandoned, which is a division of application No. 12/233,751, filed on Sep. 19, 2008, now Pat. No. 8,722,710.

(60) Provisional application No. 60/975,193, filed on Sep. 26, 2007.

(51) Int. Cl.
*A61K 31/4436* (2006.01)
*A61K 31/4439* (2006.01)
*C07D 417/12* (2006.01)

(52) U.S. Cl.
CPC ........ *A61K 31/4439* (2013.01); *C07D 417/12* (2013.01); *C07B 2200/05* (2013.01)

(58) Field of Classification Search
CPC .................................... A61K 31/4436
USPC .......................................... 514/342
See application file for complete search history.

(56) References Cited

U.S. PATENT DOCUMENTS

| | | |
|---|---|---|
| 4,421,865 A | 12/1983 | Shen |
| 4,687,777 A | 8/1987 | Meguro et al. |
| 5,149,820 A | 9/1992 | Borretzen et al. |
| 5,441,971 A | 8/1995 | Sohda et al. |
| 6,191,154 B1 | 2/2001 | Landreth et al. |
| 6,221,335 B1 | 4/2001 | Foster |
| 6,334,997 B1 | 1/2002 | Foster et al. |
| 6,432,993 B1 | 8/2002 | Fujita et al. |
| 6,440,710 B1 | 8/2002 | Keinan et al. |
| 6,603,008 B1 | 8/2003 | Ando et al. |
| 6,706,746 B2 | 3/2004 | Fujita et al. |
| 7,517,990 B2 | 4/2009 | Ito et al. |
| 8,067,450 B2 | 11/2011 | Colca et al. |
| 8,236,786 B2 | 8/2012 | Finch et al. |
| 8,263,631 B2 | 9/2012 | Fujiwara et al. |
| 8,389,556 B2 | 3/2013 | Colca et al. |
| 8,722,710 B2 | 5/2014 | Czarnik |
| 8,969,581 B2 | 3/2015 | DeWitt |
| 9,123,444 B2 | 9/2015 | Subramaniam et al. |
| 9,416,117 B2 | 8/2016 | DeWitt |
| 9,782,395 B2 | 10/2017 | Garcia Collazo et al. |
| 9,833,445 B2 | 12/2017 | DeWitt |
| 9,925,175 B2 | 3/2018 | Czarnik |
| 2003/0181494 A1 | 9/2003 | Neogi et al. |
| 2004/0253180 A1 | 12/2004 | Foster et al. |
| 2007/0082929 A1 | 4/2007 | Gant et al. |
| 2007/0197695 A1 | 8/2007 | Potyen et al. |
| 2009/0028868 A1 | 1/2009 | Fujiwara et al. |
| 2009/0076093 A1 | 3/2009 | Czarnik |
| 2009/0082405 A1 | 3/2009 | Czarnik |
| 2012/0015982 A1 | 1/2012 | Colca et al. |
| 2014/0221369 A1 | 8/2014 | DeWitt |
| 2014/0243377 A1 | 8/2014 | Czarnik |
| 2014/0275180 A1 | 9/2014 | DeWitt |
| 2015/0284346 A1 | 10/2015 | DeWitt |
| 2016/0331737 A1 | 11/2016 | DeWitt et al. |
| 2016/0354355 A1 | 12/2016 | Czarnik |
| 2017/0049762 A1 | 2/2017 | DeWitt |
| 2018/0117026 A1 | 5/2018 | DeWitt et al. |
| 2018/0118730 A1 | 5/2018 | DeWitt et al. |
| 2018/0125827 A1 | 5/2018 | DeWitt et al. |
| 2018/0125834 A1 | 5/2018 | DeWitt et al. |
| 2018/0133204 A1 | 5/2018 | DeWitt |

FOREIGN PATENT DOCUMENTS

| | | |
|---|---|---|
| EP | 1628646 B1 | 7/2010 |
| WO | WO-92/018501 A1 | 10/1992 |
| WO | WO-1995/26325 A2 | 10/1995 |
| WO | WO-1999/018081 A1 | 4/1999 |
| WO | WO-2003/033494 A1 | 4/2003 |
| WO | WO-2003/059271 A2 | 7/2003 |
| WO | WO-2004/073622 A2 | 9/2004 |
| WO | WO-2005/058827 A1 | 6/2005 |
| WO | WO-2006/064826 A1 | 6/2006 |
| WO | WO-2006/083781 A1 | 8/2006 |
| WO | WO-2006/126673 A1 | 11/2006 |
| WO | WO-2007/007656 A1 | 1/2007 |
| WO | WO-2007/100027 A1 | 9/2007 |
| WO | WO-2007/109024 A2 | 9/2007 |
| WO | WO-2007/136129 A1 | 11/2007 |
| WO | WO-2008/099944 A1 | 8/2008 |

(Continued)

OTHER PUBLICATIONS

Aithal et al., "Randomized, Placebo-Controlled Trial of Pioglitazone in Nondiabetic Subjects with Nonalcoholic Steatohepatitis," *Gastroenterology* (2008), vol. 135, pp. 1176-1184.

Baillie, T., "The Use of Stable Isotopes in Pharmacological Research", Pharmacological Reviews, 33(2):81-132 (1981).

Bharatam et al., "Rapid Racemization in Thiazolidinediones: A Quantum Chemical Study", J. Phys. Chem. A., 108:3784-3788 (2004).

Boettcher et al., "Meta-analysis: Pioglitazone Improves Liver Histology and Fibrosis in Patients with Non-Alcoholic Steatohepatitis," Aliment Pharmacol Ther, vol. 35, pp. 66-75 (2012).

(Continued)

*Primary Examiner* — Patricia L Morris
(74) *Attorney, Agent, or Firm* — Goodwin Procter LLP

(57) ABSTRACT

The present application describes deuterium-enriched pioglitazone, pharmaceutically acceptable salt forms thereof, and methods of treating using the same.

10 Claims, No Drawings

(56) References Cited

FOREIGN PATENT DOCUMENTS

| WO | WO-2009/038681 A1 | 3/2009 |
|---|---|---|
| WO | WO-2010/015818 A1 | 2/2010 |
| WO | WO-2010/150014 A1 | 12/2010 |
| WO | WO-2011/017244 A1 | 2/2011 |
| WO | WO-2011/065420 A1 | 6/2011 |
| WO | WO-2011/098799 A2 | 8/2011 |
| WO | WO-2011/098801 A1 | 8/2011 |
| WO | WO-2011/100685 A2 | 8/2011 |
| WO | WO-2011/133441 A2 | 10/2011 |
| WO | WO-2013/011402 A1 | 1/2013 |
| WO | WO-2013/056232 A2 | 4/2013 |
| WO | WO-2013/134626 A1 | 9/2013 |
| WO | WO-2014/121036 A1 | 8/2014 |
| WO | WO-2014/152843 A1 | 9/2014 |
| WO | WO-2015/109037 A1 | 7/2015 |
| WO | 2016153948 A1 | 9/2016 |

OTHER PUBLICATIONS

Browne, T., "Stable Isotope Techniques in Early Drug Development: An Economic Evaluation", J. Clin Pharmacol, 38:213-220 (1998).
Buteau, K., "Deuterated Drugs: Unexpectedly Nonobvious?", 10 J. High Tech. L. 22 (2009) (53 pages).
Cabrero et al., "Peroxisome Proliferator-Activated Receptors and the Control of Inflammation", Current Drug Target—Inflammation & Allergy, 1(3):243-248 (2002) (Abstract).
Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology (2012), vol. 55, No. 6, pp. 2005-2023.
Chen et al., "Insulin Resistance and Metabolic Derangements in Obese Mice are Ameliorated by a Novel Peroxisome Proliferator-activated Receptor γ-sparing Thiazolidinedione", J. Biol. Chem., 287(28):23537-23548 (2012).
Cherrah et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).
Colca et al., "Identification of a Mitochondrial Target of Thiazolidinedione Insulin Sensitizers (mTOT)-Relationship to Newly Identified Mitochondrial Pyruvate Carrier Proteins", PLOS One, 8(5)e61551:1-10 (2013).
Colca et al., "Identification of a Novel Mitochondrial Protein ("mitoNEET") Cross-linked Specifically by a Thiazolidinedione Photoprobe," Am. J. Physiol. Endocrinol. Metab. (2004) vol. 286, No. 2, pp. E252-E260.
Divakaruni et al., "Thiazolidinediones are Acute, Specific Inhibitors of the Mitochondrial Pyruvate Carrier," Proc Natl Acad Sci USA, (2013), 110(14):5422-7.
Dyck et al., "Effects of Deuterium Substitution on the Catabolism of β-Phenylethylamine: An In Vivo Study", J Neurochem, 46(2):399-404 (1986).
Federal Register "Examination guidelines" p. 1-34, Sep. 1, 2010.
Federico, et al., "Focus on emerging drugs for the treatment of patients with non-alcoholic fatty liver disease," World Journal of Gastroenterology (2014), vol. 20, pp. 16841-16857.
Fisher et al., "The complexities inherent in attempts to decrease drug clearance by blocking sites of CYP-mediated metabolism", Curr. Opin. Drug Disc. Dev., 9(1):101-109 (2006).
Foster, "Deuterium Isotope Effects in Studies of Drug Metabolism," Trends Pharmacol Sci, (1984), 5:524-7.
Foster, A., "Deuterium Isotope Effects in the Metabolism of Drugs and Xenobiotics: Implications for Drug Design", Adv. Drug Res., 14:2-40 (1985).
Gouyette, A., "Synthesis of Deuterium-labelled Elliptinium and its Use in Metabolic Studies", Biomedical and Environmental Mass Spectrometry, 15:243-247 (1988).

Harbeson et al., "Deuterium in Drug Discovery and Development", Annual Reports in Med Chem, 46:403-417 (2011).
Haskins, N. J. "The Application of Stable Isotopes in Biomedical Research," Biomedical Mass Spectrometry, 9 (7), 1982, 269-277.
Honma et al. "The Metabolism of Roxatidine Acetate Hydrochloride", Drug Metabolism and Disposition, 15(4):551-559 (1987).
Hutt et al., "The Chiral Switch: The Development of Single Enantiomer Drugs from Racemates", ACTA Facult. Pharm. Univ. Comenianae, 50:7-23 (2003).
International Search Report and Written Opinion for International Application No. PCT/US2015/011493 dated Mar. 6, 2015 (10 pages).
International Search Report and Written Opinion for PCT/US2014/014083 dated May 16, 2014 (12 pages).
International Search Report and Written Opinion for PCT/US2014/027943 dated Jul. 10, 2014 (15 pages).
Jaakkola et al., "Montelukast and Zafirlukast do not Affect the Pharmacokinetics of the CYP2C8 Substrate Pioglitazone," Eur J Clin Pharmacol, (2006), 62(7):503-9.
Jaakkola et al., "Pioglitazone is Metabolized by CYP2C8 and CYP3A4 in vitro. Potential for Interactions with CYP2C8 Inhibitors," Basic Clin Phamacol Toxicol, (2006), 99(1):44-51.
Jamali et al., "Investigation of racemisation of the enantiomers of glitazone drug compounds at different pH using chiral HPLC and chiral CE", J. Pharm. and Biomed. Anal., 46:82-87 (2008).
Kaufman et al., "Deuterium Enrichment of Vitamin A at the C20 Position Slows the Formation of Detrimental Vitamin A Dimers in Wild-type Rodents", J. Biol. Chem., 286(10):7958-7965 (2011).
Kawaguchi et al., "Pioglitazone prevents hepatic steatosis, fibrosis, and enzyme-altered lesions in rat liver cirrhosis induced by a choline-deficient L-amino acid-defined diet," Biochemical and Biophysical Research Communications, (2004), vol. 315, pp. 187-195.
Kawai et al., "Hydrogen-Rich Water Prevents Progression of Nonalcoholic Steatohepatitis and Accompanying Hepatocarcinogenesis in Mice," Hepatology (2012), vol. 56, pp. 912-921.
Kushner, D.J. et al. "Pharmacological Uses and Perspectives of Heavy Water and Deuterated Compounds," Canadian Journal of Physiology and Pharmacology, 1999, 77(2), 79-88.
Leclercq et al., "Intrahepatic insulin resistance in a murine model of steatohepatitis: effect of PPARγ agonist pioglitazone," Laboratory Investigation (2007), vol. 87, pp. 56-65.
Lin et al., "Dose effect of thiazolidinedione on cancer risk in type 2 diabetes mellitus patients: a six-year population-based cohort study," Journal of Clinical Pharmacy and Therapeutics (2014), vol. 39, pp. 354-360.
Lomonaco et al., "Nonalcoholic Fatty Liver Disease: Current Issues and Novel Treatment Approaches," Drugs, vol. 73, pp. 1-14 (2013).
Lutchman et al., "The Effects of Discontinuing Pioglitazone in Patients with Nonalcoholic Steatohepatitis," Hepatology (2007) vol. 46, pp. 424-429.
Maltais et al., "In Vitro and In Vivo Isotope Effects with Hepatitis C Protease Inhibitors: Enhanced Plasma Exposure of Deuterated Telaprevir versus Telaprevir in Rats", J. Med. Chem. (2009) vol. 52, pp. 7993-8001.
Mislow et al., "A Note on Steric Isotope Effects. Conformational Kinetic Isotope Effects in the Racemization of 9,10-Dihydro-4,5-Dimethylphenanthrene", J. Am. Chem. Soc. 85:1199-1200 (1963).
Motani et al., "INT131: A Selective Modulator of PPARγ", J. Mol. Biol., 386:1301-1311 (2009).
Nassar et al., "Improving the decision-making process in the structural modification of drug candidates: enhancing metabolic stability", Drug Discovery Today, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", Drug Metabolism and Disposition, 31(12):1481-1498 (2003).
Parks et al., "Differential Activity of Rosiglitazone Enantiomers at PPARγ", Bioorg. & Medicinal Chem. Letters, 8:3657-3658 (1998).
Pfutzner et al., "Pioglitazone: update on an oral antidiabetic drug with antiatherosclerotic effects", Expert Opin. Pharmacother., 8(12):1985-1998 (2007).

(56) References Cited

OTHER PUBLICATIONS

Pieniaszek, Jr., et al., "Moricizine Bioavailability via Simultaneous, Dual, Stable Isotope Administration: Bioequivalence Implications", J Clin Pharmacol, 39:817-825 (1999).
Promrat et al., "A Pilot Study of Pioglitazone Treatment for Nonalcoholic Steatohepatitis," Hepatology (2004), vol. 39, pp. 188-196.
Sanyal et al., "A Pilot Study of Vitamin E Versus Vitamin E and Pioglitazone for the Treatment of Nonalcoholic Steatohepatitis," *Clinical Gastroenterology and Hepatology* (2004), vol. 2, pp. 1107-1115.
Sanyal et al., "Pioglitazone, Vitamin E, or Placebo for Nonalcoholic Steatohepatitis," *The New England Journal of Medicine*, (2010) vol. 362, pp. 1675-1685.
Shao, L. & Hewitt, M.C. "The Kinetic Isotope Effect in the Search for Deuterated Drugs," *Drug News & Perspectives*, 2010, vol. 23, No. 6, pp. 398-404.
Shao et al., "Derivatives of tramadol for increased duration of effect", Bioorg. Med. Chem. Lett. 16:691-694 (2006).
Smith et al., "Non-Alcoholic Fatty Liver Disease," Critical Reviews in Clinical Laboratory Sciences, vol. 48, pp. 97-113 (2011).
Sohda et al., "Studies on Antidiabetic Agents. XII.1) Synthesis and Activity of the metabolites of (±)-5-[p-[2-(5-Ethyl-2-pyridypethoxy]benzyl]-2,4-thiazolidinedione (Pioglitazone)", Chem. Pharm. Bull., 43(12):2168-2172 (1995).
Stedman and Barclay, "Review Article: Comparison of the Pharmacokinetics, Acid Suppression and Efficacy of Proton Pump Inhibitors," Aliment Pharmacol Ther, (2000), 14(8):963-78.
Tilg and Moschen, "Evolving Therapies for Non-Alcoholic Steatohepatitis," Expert Opin Drug Discov, (2014), 9(6):687-96.
Tonn et al. "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes," *Biological Mass Spectrometry*, 22 (11) 1993, 633-642.
Uto et al., "The peroxisome proliferator-activated receptor-γ agonist, pioglitazone, inhibits fat accumulation and fibrosis in the livers of rats fed a choline-deficient, L-amino acid-defined diet," *Hepatology Research* (2005), vol. 32, pp. 235-242.
Van Wagner et al., "The role of insulin-sensitizing agents in the treatment of nonalcoholic steatohepatitis," *Ther Adv Gastroenterol* (2011) vol. 4, pp. 249-263.
Wade, D., "Deuterium isotope effects on noncovalent interactions between molecules", *Chemico-Biological Interactions*, 117 p. 191-217 (1999).
Wiberg, K., "The Deuterium Isotope Effect", Chem. Rev., 55(4):713-743 (1955).
Wolen, R. L. "The application of stable isotopes to studies of drug bioavailability and bioequivalence," *J. Clin. Pharm*. (1986) vol. 26, pp. 419-424.
Yamamoto et al., "Synthesis and Configurational Stability of (S)- and (R)-Deuteriothalidomides", Chem. Pharm. Bull. 58(1):110-112 (2010).
Yarnell, A., "Heavy-Hydrogen Drugs Turn Heads, Again", Chemical & Engineering News, 87(25):36-39 (2009).
Zhang et al., "Thiazolidinediones Improve Hepatic Fibrosis in Rats with Non-Alcoholic Steatohepatitis by Activating the Adenosine Monophosphate-Activated Protein Kinase Signalling Pathway," Clinical and Experimental Pharmacology and Physiology, vol. 39, pp. 1026-1033 (2012).
Zhu Y. et al., "Deuterated Clopidogrel Analogues as a New Generation of Antiplatelet Agents", ACS Med. Chem. Lett. 2013, vol. 4, Issue 3, pp. 349-352.
Dorwald, "Side Reactions in Organic Synthesis," Wiley, pp. IX of preface pp. 1-15 (2005).
Woo, H.Y, et al., "Rescue therapy with adefovir in decompensated liver cirrhosis patients with lamivudine-resistant hepatitis B virus", Clinical and Molecular Hepatology, 2014, vol. 20, pp. 168-176.
Peng, S., et al., "An Updated Meta-Analysis of Randomized Controlled Trials Assessing the Effect of Sorafenib in Advanced Hepatocellular Carcinoma", PLOS One, 2014, vol. 9, No. 12, pp. e112530.
Farlow, M. R., et al., "Comparing Clinical Profiles in Alzheimer's Disease and Parkinson's Disease Dementia", Dementia and Geriatric Cognitive Disorders Extra, 2013, vol. 3, pp. 281-290.
Griebeler, M.L., et al, "Pharmacologic interventions for painful diabetic neuropathy: An umbrella systematic review and comparative effectiveness network meta-analysis", Annals of Internal Medicine, 2014, vol. 161, No. 9, pp. 639-649.
Zhou, C. et al., "Discovery of 5-aryloxy-2,4-thiazolidinediones as potent GPR40 agonists", Bioorg. Med. Chem. Lett. 2010, vol. 20, No. 3, pp. 1298-1301.
Christiansen, E. et al., "Identification of a Potent and Selective Free Fatty Acid Receptor 1 (FFA1/GPR40) Agonist with Favorable Physicochemical and in Vitro ADME Properties", J. Med. Chem. (2011) vol. 54, No. 19, pp. 6691-6703.
International Search Report and Written Opinion for PCT/US2015/011493 dated Mar. 6, 2015 (9 pages).
Hardy, T. et al. "Nonalcoholic fatty liver disease: new treatments," *Curr. Opin. Gastroenterology* (2015) vol. 31, No. 3, pp. 175-183.
Chalasani et al., "The Diagnosis and Management of Non-Alcoholic Fatty Liver Disease: Practice Guideline by the American Gastroenterological Association, American Association for the Study of Liver Diseases, and American College of Gastroenterology," *Gastroenterology* (2012), vol. 142, No. 7, pp. 1592-1609.
Cusi, K. et al. "Long-Term Pioglitazone Treatment for Patients With Nonalcoholic Steatohepatitis and Prediabetes or Type 2 Diabetes Mellitus: A Randomized, Controlled Trial," *Ann. Intern. Med*. published online at doi: 10.7326/M15-1774. Published in final form as *Ann. Intern. Med*. (2016) vol. 165, No. 5, p. 305-315.
Tanis, S. P. et al. "Synthesis and Biological Activity of Metabolites of the Antidiabetic, Antihyperglycemic Agent Pioglitazone," *J. Med. Chem*. (1996) vol. 39, pp. 5053-5063.
Leoni, A. et al., "Novel thiazole derivatives: a patent review (2008-2012. Part 2)," Expert Opin. Ther. Patents (2014), vol. 24, No. 7, pp. 759-777.
Jorden, D., "World Alzheimer Day: French Doctor Denounces Routine Alzheimer Medications," dated Dec. 20, 2015. Downloaded from the Internet at URL: https://zcomm.org/znetarticle/world-alzheimer-day-french-doctor-denounces-routine-alzheimer-medications/ (4 pages).
Landreth, G. et al., "PPARγ Agonists as Therapeutics for the Treament of Alzheimer's Disease," *Neurotherapeutics: J. Am. Soc. Exper. NeuroTherapeutics* (2008), vol. 5, No. 3, pp. 481-489.
Polyzos, S. A. and Mantzoros, C. S. "Adiponectin as a target for the treament of nonalcoholic steatohepatitis with thiazolidinediones: A systematic review," *Metabolism, Clinical and Experimental* (2016), vol. 65, No. 9, pp. 1297-1306.
World Health Organization "The ICD-10 Classification of Mental and Behavioural Disorders: Diagnostic criteria for research," Geneva (1993).
Venkatesh, S. and Lipper, R. A., "Role of the Development Scientist in Compound Lead Selection and Optimization," *J. Pharm. Sci*. (2000), vol. 89, No. 2, pp. 145-154.
Mandard, S. and Patsouris, D., "Nuclear Control of the Inflammatory Response in Mammals by Peroxisome Proliferator-Activated Receptors," *PPAR Research* (2013) Article ID 613864, DOI: 10.1155/2013/613864. (23 pages).
Binda, C. et al., "Molecular Insights into Human Monoamine Oxidase B Inhibition by the Glitazone Antidiabetes Drugs," *ACS Med. Chem. Lett*. (2012), vol. 3, pp. 39-42.

DEUTERIUM-ENRICHED PIOGLITAZONE

CROSS-REFERENCE TO RELATED APPLICATIONS

The present application is a divisional of U.S. patent application Ser. No. 15/088,472, filed Apr. 1, 2016, which is a continuation of U.S. patent application Ser. No. 14/272,761, filed May 8, 2014, which is a divisional of U.S. patent application Ser. No. 12/233,751, filed on Sep. 19, 2008, which claims priority to U.S. Provisional Patent Application Ser. No. 60/975,193, filed Sep. 26, 2007; the entire disclosure of each of which is hereby incorporated by reference.

FIELD OF THE INVENTION

This invention relates generally to deuterium-enriched pioglitazone, pharmaceutical compositions containing the same, and methods of using the same.

BACKGROUND OF THE INVENTION

Pioglitazone, shown below, is a well known thiazolidinedione.

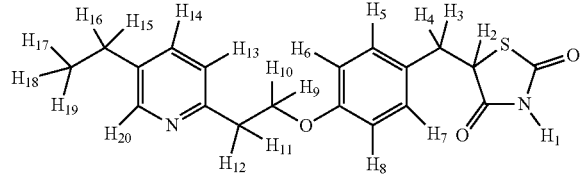

Since pioglitazone is a known and useful pharmaceutical, it is desirable to discover novel derivatives thereof. Pioglitazone is described in U.S. Pat. No. 4,687,777; the contents of which are incorporated herein by reference.

SUMMARY OF THE INVENTION

Accordingly, one object of the present invention is to provide deuterium-enriched pioglitazone or a pharmaceutically acceptable salt thereof.

It is another object of the present invention to provide pharmaceutical compositions comprising a pharmaceutically acceptable carrier and a therapeutically effective amount of at least one of the deuterium-enriched compounds of the present invention or a pharmaceutically acceptable salt thereof.

It is another object of the present invention to provide a method for treating a disease selected from diabetes mellitus type 2 and/or non-alcoholic steatohepatitis, comprising administering to a host in need of such treatment a therapeutically effective amount of at least one of the deuterium-enriched compounds of the present invention or a pharmaceutically acceptable salt thereof.

It is another object of the present invention to provide a novel deuterium-enriched pioglitazone or a pharmaceutically acceptable salt thereof for use in therapy.

It is another object of the present invention to provide the use of a novel deuterium-enriched pioglitazone or a pharmaceutically acceptable salt thereof for the manufacture of a medicament (e.g., for the treatment of diabetes mellitus type 2 and/or non-alcoholic steatohepatitis).

These and other objects, which will become apparent during the following detailed description, have been achieved by the inventor's discovery of the presently claimed deuterium-enriched pioglitazone.

DETAILED DESCRIPTION OF PREFERRED EMBODIMENTS

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

The present invention provides deuterium-enriched pioglitazone or a pharmaceutically acceptable salt thereof. There are twenty hydrogen atoms in the pioglitazone portion of pioglitazone as show by variables $R_1$-$R_{20}$ in formula I below.

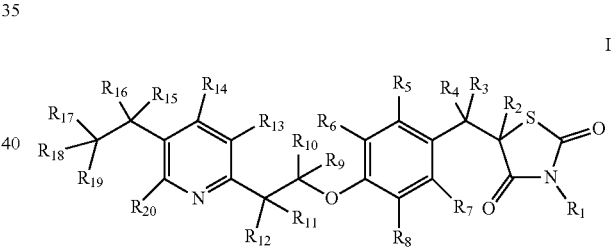

I

The hydrogens present on pioglitazone have different capacities for exchange with deuterium. Hydrogen atom $R_1$ is easily exchangeable under physiological conditions and, if replaced by a deuterium atom, it is expected that it will readily exchange for a proton after administration to a patient. Hydrogen atom R2 may be exchanged for a deuterium atom by the action of $D_2SO_4$/$D_2O$ or NaOD/$D_2O$. The remaining hydrogen atoms are not easily exchangeable for deuterium atoms. However, deuterium atoms at the remaining positions may be incorporated by the use of deuterated starting materials or intermediates during the construction of pioglitazone.

The present invention is based on increasing the amount of deuterium present in pioglitazone above its natural abundance. This increasing is called enrichment or deuterium-enrichment. If not specifically noted, the percentage of enrichment refers to the percentage of deuterium present in the compound, mixture of compounds, or composition. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Since there are 20 hydrogens in pioglitazone, replacement of a single hydrogen atom with deuterium would result in a molecule with about 5% deuterium enrichment. In order to achieve enrichment less than about 5%, but above the natural abundance, only partial deuteration of one site is required. Thus, less than about 5% enrichment would still refer to deuterium-enriched pioglitazone.

With the natural abundance of deuterium being 0.015%, one would expect that for approximately every 6,667 molecules of pioglitazone (1/0.00015=6,667), there is one naturally occurring molecule with one deuterium present. Since pioglitazone has 20 positions, one would roughly expect that for approximately every 133,340 molecules of pioglitazone (20×6,667), all 20 different, naturally occurring, monodeuterated pioglitazones would be present. This approximation is a rough estimate as it doesn't take into account the different exchange rates of the hydrogen atoms on pioglitazone. For naturally occurring molecules with more than one deuterium, the numbers become vastly larger. In view of this natural abundance, the present invention, in an embodiment, relates to an amount of an deuterium enriched compound, whereby the enrichment recited will be more than naturally occurring deuterated molecules.

In view of the natural abundance of deuterium-enriched pioglitazone, the present invention also relates to isolated or purified deuterium-enriched pioglitazone. The isolated or purified deuterium-enriched pioglitazone is a group of molecules whose deuterium levels are above the naturally occurring levels (e.g., 5%). The isolated or purified deuterium-enriched pioglitazone can be obtained by techniques known to those of skill in the art (e.g., see the syntheses described below).

The present invention also relates to compositions comprising deuterium-enriched pioglitazone. The compositions require the presence of deuterium-enriched pioglitazone which is greater than its natural abundance. For example, the compositions of the present invention can comprise (a) a μg of a deuterium-enriched pioglitazone; (b) a mg of a deuterium-enriched pioglitazone; and, (c) a gram of a deuterium-enriched pioglitazone.

In an embodiment, the present invention provides an amount of a novel deuterium-enriched pioglitazone.

Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another embodiment, the present invention provides a novel, deuterium enriched compound of formula I or a pharmaceutically acceptable salt thereof.

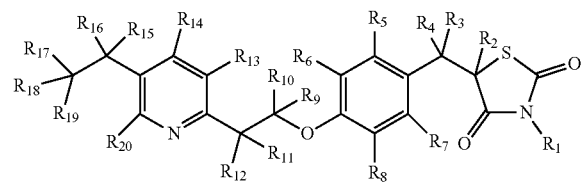

I wherein $R_1$-$R_{20}$ are independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j) at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides a novel, deuterium enriched compound of formula I or a phaititaceutically acceptable salt thereof, wherein the abundance of deuterium in $R_1$ is at least 100%.

In another embodiment, the present invention provides a novel, deuterium enriched compound of formula 1 or a pharmaceutically acceptable salt thereof, wherein the abundance of deuterium in $R_2$ is at least 100%.

In another embodiment, the present invention provides a novel, deuterium enriched compound of foiinula I or a pharmaceutically acceptable salt thereof, wherein the abundance of deuterium in $R_1$-$R_2$ is at least 50%. The abundance can also be (a) 100%.

In another embodiment, the present invention provides a novel, deuterium enriched compound of formula I or a pharmaceutically acceptable salt thereof, wherein the abundance of deuterium in $R_3$-$R_4$ is at least 50%. The abundance can also be (a) 100%.

In another embodiment, the present invention provides a novel, deuterium enriched compound of formula 1 or a pharmaceutically acceptable salt thereof, wherein the abundance of deuterium in $R_5$-$R_8$ is at least 25%. The abundance can also be (a) at least 50%, (b) at least 75%, and (c) 100%.

In another embodiment, the present invention provides a novel, deuterium enriched compound of formula I or a pharmaceutically acceptable salt thereof, wherein the abundance of deuterium in $R_9$-$R_{12}$ is at least 25%. The abundance can also be (a) at least 50%, (b) at least 75%, and (e) 100%.

In another embodiment, the present invention provides a novel, deuterium enriched compound of formula I or a pharmaceutically acceptable salt thereof, wherein the abundance of deuterium in $R_{13}$-$R_{14}$ and $R_{20}$ is at least 33%. The abundance can also be (a) at least 67%, and (b) 100%.

In another embodiment, the present invention provides a novel, deuterium enriched compound of formula I or a pharmaceutically acceptable salt thereof, wherein the abundance of deuterium in $R_{15}$-$R_{19}$ is at least 20%. The abundance can also be (a) at least 40%, (b) at least 60%, (c) at least 80%, and (d) 100%.

In another embodiment, the present invention provides an isolated novel, deuterium enriched compound of formula I or a pharmaceutically acceptable salt thereof.

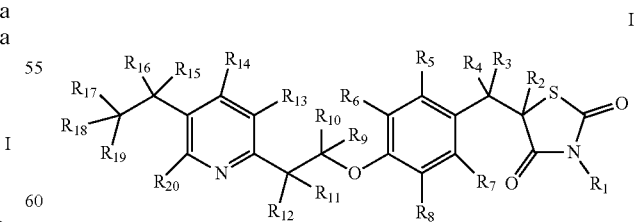

I wherein $R_1$-$R_{20}$ arc independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j)

at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides an isolated novel, deuterium enriched compound of formula 1 or a pharmaceutically acceptable salt thereof, wherein the abundance of deuterium in $R_1$ is at least 100%.

In another embodiment, the present invention provides an isolated novel, deuterium enriched compound of formula I or a pharmaceutically acceptable salt thereof, wherein the abundance of deuterium in $R_2$ is at least 100%.

In another embodiment, the present invention provides an isolated novel, deuterium enriched compound of formula I or a pharmaceutically acceptable salt thereof, wherein the abundance of deuterium in $R_1$-$R_2$ is at least 50%. The abundance can also be (a) 100%.

In another embodiment, the present invention provides an isolated novel, deuterium enriched compound of formula 1 or a pharmaceutically acceptable salt thereof, wherein the abundance of deuterium in $R_3$-$R_4$ is at least 50%. The abundance can also be (a) 100%.

In another embodiment, the present invention provides an isolated novel, deuterium enriched compound of formula I or a pharmaceutically acceptable salt thereof, wherein the abundance of deuterium in $R_5$-$R_8$ is at least 25%. The abundance can also be (a) at least 50%, (b) at least 75%, and (c) 100%.

In another embodiment, the present invention provides an isolated novel, deuterium enriched compound of formula I or a pharmaceutically acceptable salt thereof, wherein the abundance of deuterium in $R_9$-$R_{12}$ is at least 25%. The abundance can also be (a) at least 50%, (b) at least 75%, and (c) 100%.

In another embodiment, the present invention provides an isolated novel, deuterium enriched compound of formula I or a pharmaceutically acceptable salt thereof, wherein the abundance of deuterium in $R_{13}$-$R_{14}$ and $R_{20}$ is at least 33%. The abundance can also be (a) at least 67%, and (b) 100%.

In another embodiment, the present invention provides an isolated novel, deuterium enriched compound of formula I or a pharmaceutically acceptable salt thereof, wherein the abundance of deuterium in $R_{15}$-$R_{19}$ is at least 20%. The abundance can also be (a) at least 40%, (b) at least 60%, (c) at least 80%, and (d) 100%.

In another embodiment, the present invention provides novel mixture of deuterium enriched compounds of formula I or a pharmaceutically acceptable salt thereof.

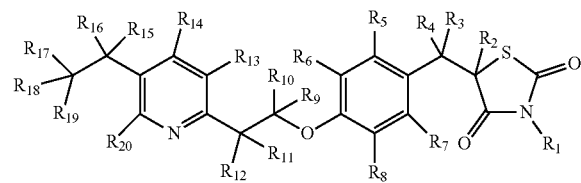

I wherein $R_1$-$R_{20}$ are independently selected from H and D; and the abundance of deuterium in $R_1$-$R_{20}$ is at least 5%. The abundance can also be (a) at least 10%, (b) at least 15%, (c) at least 20%, (d) at least 25%, (e) at least 30%, (f) at least 35%, (g) at least 40%, (h) at least 45%, (i) at least 50%, (j) at least 55%, (k) at least 60%, (l) at least 65%, (m) at least 70%, (n) at least 75%, (o) at least 80%, (p) at least 85%, (q) at least 90%, (r) at least 95%, and (s) 100%.

In another embodiment, the present invention provides a novel mixture of, deuterium enriched compound of formula I or a pharmaceutically acceptable salt thereof, wherein the abundance of deuterium in $R_1$ is at least 100%.

In another embodiment, the present invention provides a novel mixture of, deuterium enriched compound of formula I or a pharmaceutically acceptable salt thereof, wherein the abundance of deuterium in $R_2$ is at least 100%.

In another embodiment, the present invention provides a novel mixture of, deuterium enriched compound of formula I or a pharmaceutically acceptable salt thereof, wherein the abundance of deuterium in $R_1$-$R_2$ is at least 50%. The abundance can also be (a) 100%.

In another embodiment, the present invention provides a novel mixture of, deuterium enriched compound of formula I or a pharmaceutically acceptable salt thereof, wherein the abundance of deuterium in $R_3$-$R_4$ is at least 50%. The abundance can also be (a) 100%.

In another embodiment, the present invention provides a novel mixture of, deuterium enriched compound of formula I or a pharmaceutically acceptable salt thereof, wherein the abundance of deuterium in $R_5$-$R_8$ is at least 25%. The abundance can also be (a) at least 50%, (b) at least 75%, and (c) 100%.

In another embodiment, the present invention provides a novel mixture of, deuterium enriched compound of formula I or a pharmaceutically acceptable salt thereof, wherein the abundance of deuterium in $R_9$-$R_{12}$ is at least 25%. The abundance can also be (a) at least 50%, (b) at least 75%, and (c) 100%.

In another embodiment, the present invention provides a novel mixture of, deuterium enriched compound of formula I or a pharmaceutically acceptable salt thereof, wherein the abundance of deuterium in $R_{13}$-$R_{14}$ and $R_{20}$ is at least 33%. The abundance can also be (a) at least 67%, and (b) 100%.

In another embodiment, the present invention provides a novel mixture of, deuterium enriched compound of formula I or a pharmaceutically acceptable salt thereof, wherein the abundance of deuterium in $R_{15}$-$R_{19}$ is at least 20%. The abundance can also be (a) at least 40%, (b) at least 60%, (c) at least 80%, and (d) 100%.

In another embodiment, the present invention provides novel pharmaceutical compositions, comprising: a pharmaceutically acceptable carrier and a therapeutically effective amount of a deuterium-enriched compound of the present invention.

In another embodiment, the present invention provides a novel method for treating a disease selected from diabetes mellitus type 2 and/or non-alcoholic steatohepatitis comprising: administering to a patient in need thereof a therapeutically effective amount of a deuterium-enriched compound of the present invention.

In another embodiment, the present invention provides an amount of a deuterium-enriched compound of the present invention as described above for use in therapy.

In another embodiment, the present invention provides the use of an amount of a deuterium-enriched compound of the present invention for the manufacture of a medicament (e.g., for the treatment of diabetes mellitus type 2 and/or non-alcoholic steatohepatitis).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds of the present invention may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present invention.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

EXAMPLES

Table 1 provides compounds that are representative examples of the present invention. When one of $R_1$-$R_{20}$ is present, it is selected from H or D.

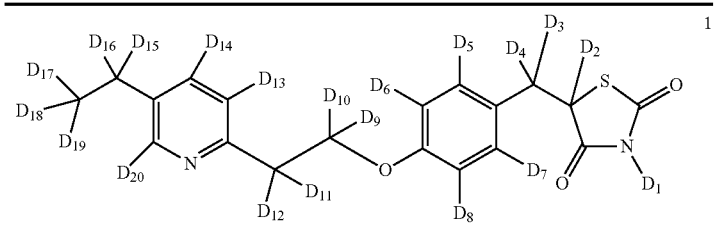

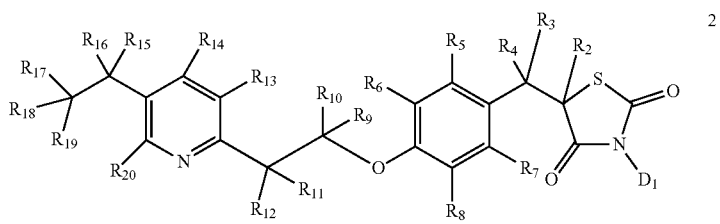

-continued
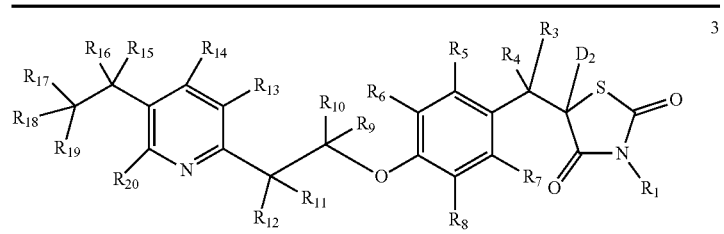
3
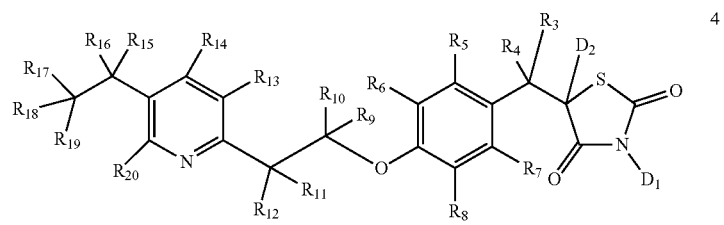
4
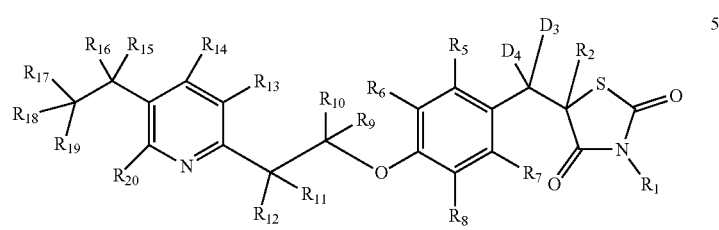
5
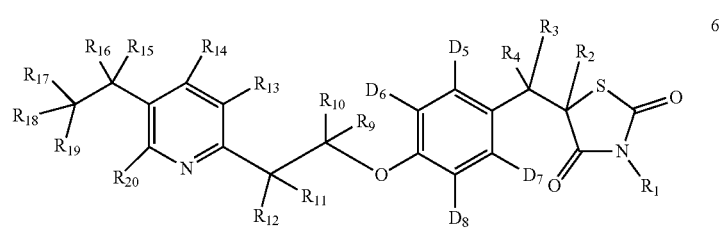
6
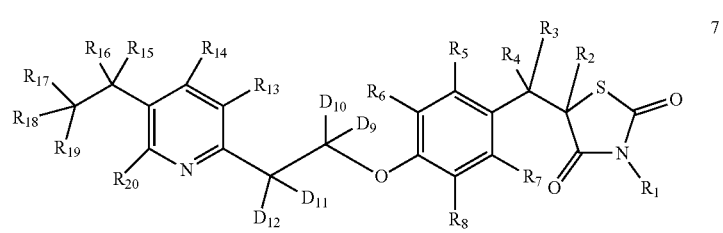
7
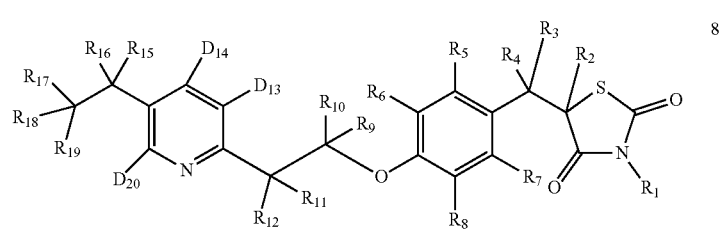
8
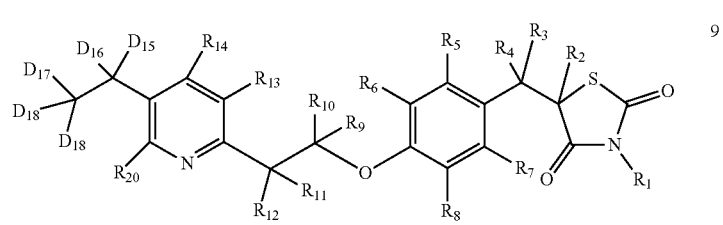
9

Table 2 provides compounds that are representative examples of the present invention. Where H is shown, it represents naturally abundant hydrogen.
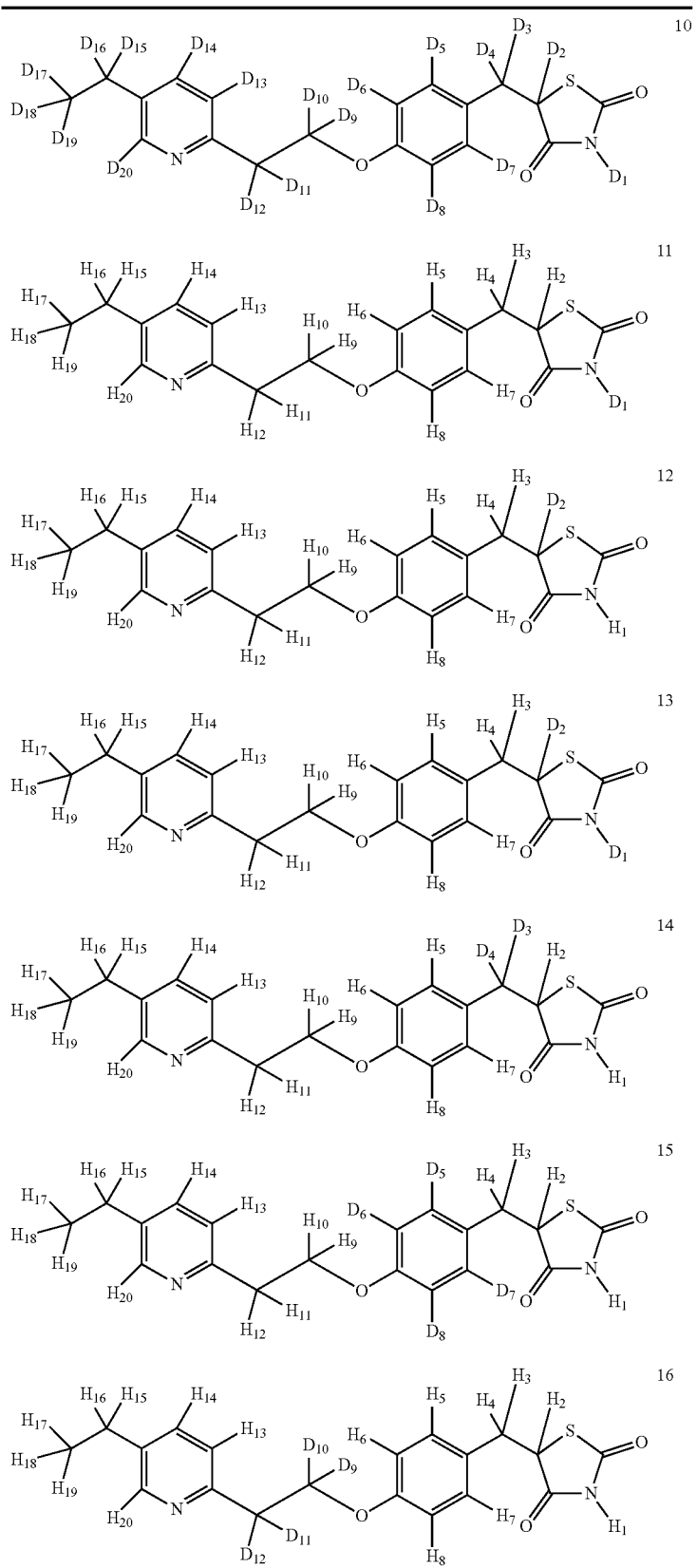

-continued

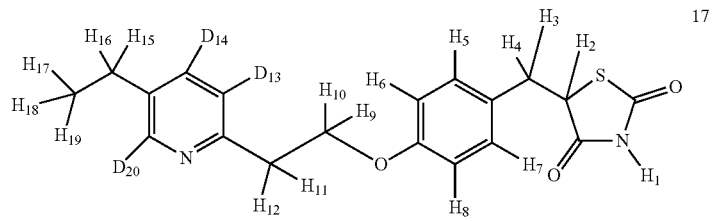

17

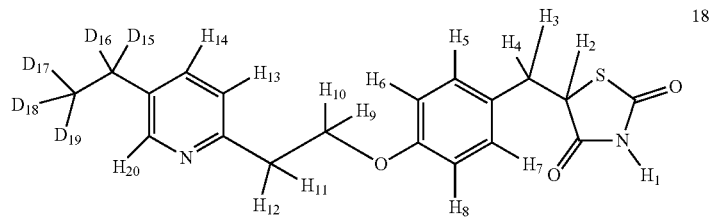

18

Numerous modifications and variations of the present invention are possible in light of the above teachings. It is therefore to be understood that within the scope of the appended claims, the invention may be practiced otherwise that as specifically described herein,

The invention claimed is:

1. A method of treating diabetes mellitus type 2, comprising administering a therapeutically effective amount of a deuterium-enriched compound of formula I to a patient in need thereof to treat the diabetes mellitus type 2, wherein formula I is represented by:

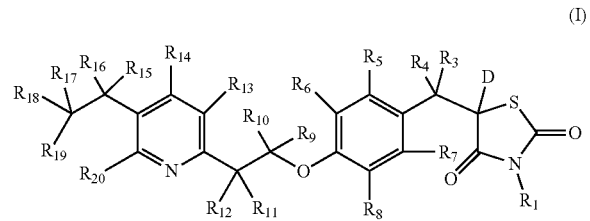

(I)

or pharmaceutically acceptable salt thereof, wherein $R_1$ and $R_3$-$R_{20}$ are independently H or D.

2. The method of claim 1, wherein $R_1$ and $R_3$-$R_{20}$ are H.

3. The method of claim 1, wherein the deuterium-enriched compound is

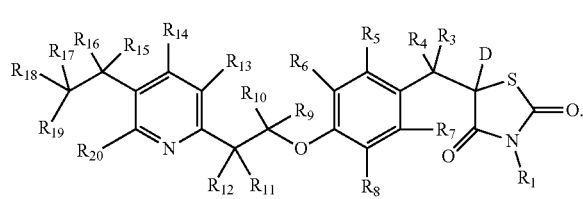

4. The method of claim 3, wherein $R_1$ and $R_3$-$R_{20}$ are H.

5. The method of claim 1, wherein the deuterium-enriched compound is represented by

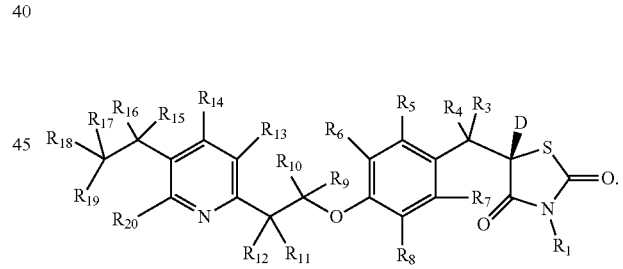

or pharmaceutically acceptable salt thereof.

6. The method of claim 5, wherein $R_1$ and $R_3$-$R_{20}$ are H.

7. The method of claim 1, wherein the deuterium-enriched compound is

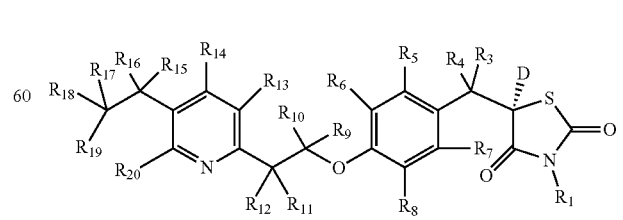

8. The method of claim 1, wherein the deuterium-enriched compound is represented by or pharmaceutically acceptable salt thereof.

9. The method of claim 8, wherein $R_1$ and $R_3$-$R_{20}$ are H.
10. The method of claim 1, wherein the deuterium-enriched compound is
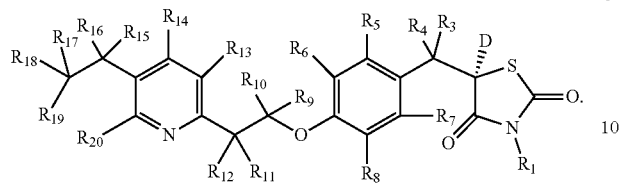
* * * * *